United States Patent
Meschisen et al.

(10) Patent No.: US 8,256,679 B2
(45) Date of Patent: Sep. 4, 2012

(54) USE OF BARCODE MENUS TO CONFIGURE AND SET-UP VITAL SIGNS MONITORS

(75) Inventors: Kathleen R. Meschisen, Acton, MA (US); Martin K. Mason, Andover, MA (US); Joseph R. Fallon, Boxford, MA (US); Richard James Conrad, Hamilton, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 395 days.

(21) Appl. No.: 12/595,262

(22) PCT Filed: Mar. 28, 2008

(86) PCT No.: PCT/IB2008/051169
§ 371 (c)(1),
(2), (4) Date: Oct. 9, 2009

(87) PCT Pub. No.: WO2008/125997
PCT Pub. Date: Oct. 23, 2008

(65) Prior Publication Data
US 2010/0056883 A1    Mar. 4, 2010

Related U.S. Application Data

(60) Provisional application No. 60/911,292, filed on Apr. 12, 2007.

(51) Int. Cl.
*G06K 7/10* (2006.01)
(52) U.S. Cl. .............. 235/462.15; 235/462.25
(58) Field of Classification Search ........... 235/462.01–462.45, 472.01–472.03; 340/539.12; 600/509, 515
See application file for complete search history.

(56) References Cited

U.S. PATENT DOCUMENTS

| | | | |
|---|---|---|---|
| 4,825,058 A | 4/1989 | Poland | |
| 5,034,598 A * | 7/1991 | Poland | 235/435 |
| 5,120,943 A | 6/1992 | Benz | |
| 5,361,755 A | 11/1994 | Schraag et al. | |
| 6,088,695 A | 7/2000 | Kara | |
| 6,167,290 A * | 12/2000 | Yang et al. | 600/322 |
| 6,321,989 B1 | 11/2001 | Wilz, Sr. et al. | |
| 6,475,146 B1 | 11/2002 | Frelburger et al. | |
| 6,565,005 B1 * | 5/2003 | Wilz et al. | 235/462.25 |
| 8,066,187 B2 * | 11/2011 | Zsigmond et al. | 235/462.01 |
| 2003/0125986 A1 | 7/2003 | Collosi | |
| 2003/0197366 A1 | 10/2003 | Kusterbeck | |
| 2004/0078333 A1 | 4/2004 | Hilton et al. | |
| 2004/0184109 A1 | 9/2004 | Short et al. | |

(Continued)

FOREIGN PATENT DOCUMENTS
EP    1734733 A2    12/2006
(Continued)

*Primary Examiner* — Thien M Le

(57) ABSTRACT

When configuring multiple patient monitors (12) in a healthcare environment, configuration is simplified and setup time is reduced by employing barcoded configuration information that is scanned into the monitors (12) using a barcode scanner (14). A first monitor (12a) is configured by selectively scanning one or more barcodes contained in a configuration booklet. Once the first monitor (12a) is configured, its configuration information is stored and printed in barcoded format. The printed barcodes are then scanned into a second patient monitor (12b), without requiring the user to navigate the configuration barcode booklet a second time. Additionally, a patient's ID barcode is printed on vital signs records generated by the monitor, such as by a strip chart recorder or printer (20).

19 Claims, 5 Drawing Sheets

| U.S. PATENT DOCUMENTS | | | | FOREIGN PATENT DOCUMENTS | | |
|---|---|---|---|---|---|---|
| 2005/0197191 A1 | 9/2005 | McKinley et al. | | WO | 0199395 A1 | 12/2001 |
| 2005/0224571 A1 | 10/2005 | Kelley et al. | | WO | 0239341 A1 | 5/2002 |
| 2006/0000910 A1 | 1/2006 | Chong et al. | | WO | 2006016340 A1 | 2/2006 |
| 2007/0060302 A1 | 3/2007 | Fabbri | | WO | 2006058151 A2 | 6/2006 |
| 2007/0069887 A1 * | 3/2007 | Welch et al. | 340/539.12 | * cited by examiner | | |

…

USE OF BARCODE MENUS TO CONFIGURE AND SET-UP VITAL SIGNS MONITORS

CROSS REFERENCE TO RELATED APPLICATIONS

This application claims the benefit of U.S. provisional application Ser. No. 60/911,292 filed Apr. 12, 2007, which is incorporated herein by reference.

The present application finds particular application in patient healthcare systems, particularly involving vital signs monitors. However, it will be appreciated that the described technique may also find application in other types of monitors or devices, other monitoring scenarios, or other device configuration techniques.

Ease of medical equipment use is a high priority for clinicians. It is likely that an institution purchasing medical equipment will desire to customize monitor configuration to facilitate and/or accommodate desired operation and/or functionality. Often, setup needs to be repeated for multiple pieces of equipment purchased. Moreover, with the new United States CMS/HIPPA regulations and other world-wide patient information security regulations, it is necessary for medical equipment manufacturers to devise ways to protect patient information. This is especially true for hardcopy output.

In healthcare environments, it is desirable and often imperative to keep records of patient condition in order to facilitate diagnosing and managing patient illness. For instance, patient ID information is often appended to hard-copy documents, such as X-rays, patient monitor printouts, and the like. However, conventional methods for appending patient ID information often includes simply attaching the patient's name to the document, which does not protect the patient from prying eyes. There is an unmet need in the art for systems and methods that overcome the above-referenced problems and others.

In accordance with one aspect, a system for configuring multiple patient monitors includes a first vital signs monitor, and a first barcode scanner that reads configuration barcodes comprising configuration information and provides the configuration information to the first vital signs monitor. The system further includes a printer that generates a printout of configuration barcodes comprising information related to the configuration of the first vital signs monitor.

In accordance with another aspect, a method of configuring multiple vital signs monitors includes configuring a first vital signs monitor, storing configuration information in the first vital signs monitor when configuration is complete, and printing the stored configuration information in the form of one or more barcodes. The method further includes configuring a second vital signs monitor by scanning the printed barcodes with a second barcode scanner coupled to the second vital signs monitor.

Another aspect relates to a system that facilitates configuring multiple patient monitoring devices, including means for configuring a first patient monitoring device, means for storing configuration information, and means for printing barcodes comprising configuration information. The system further includes means for configuring a second patient monitoring device by scanning the printed barcodes.

Another aspect relates to a patient monitor comprising a plurality of inputs for receiving each of a plurality of vital sign readings, a memory for recording the received vital sign readings, a user input device, and a barcode reader. The monitor further includes a configuration processor for configuring the monitor to receive selected vital signs, and threshold values for at least some of the selected vital signs, the configuration processor being connected with the barcode reader and the user interface to receive configuration instructions therefrom, and a barcode printer connected with the configuration processor to print configuration instructions for other monitors in barcode format.

One advantage resides in reducing configuration time for multiple monitors.

Another advantage resides in mitigating human error that can occur when entering configuration information into a monitor.

Still further advantages of the subject innovation will be appreciated by those of ordinary skill in the art upon reading and understand the following detailed description.

The innovation may take form in various components and arrangements of components, and in various steps and arrangements of steps. The drawings are only for purposes of illustrating various aspects and are not to be construed as limiting the invention.

Figure 1:
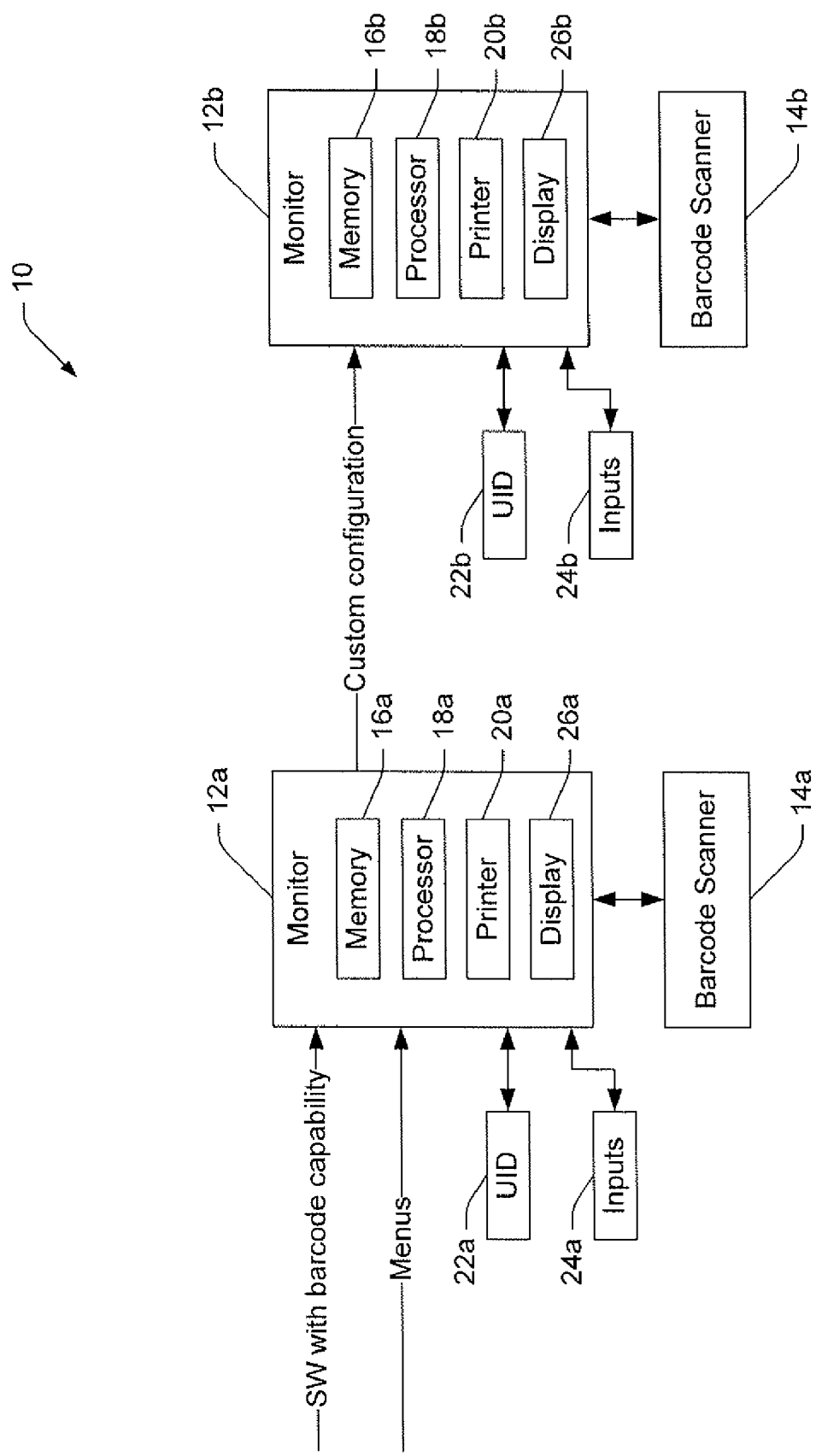
FIG. 1 illustrates a system for configuring multiple patient monitors using a barcode scanner that reads barcodes in order to simplify monitor configuration and improve patient privacy, in accordance with one or more embodiments described herein.

FIG. 1 illustrates a system 10 for configuring multiple patient monitors 12 using a barcode scanner 14 that reads barcodes in order to simplify monitor configuration and improve patient privacy, in accordance with one or more embodiments described herein. Bedside patient monitors often include barcode readers which read barcodes on patient wristbands, pharmaceuticals, and the like. Typically, a healthcare provider, such as a hospital or the like, buys several dozen bedside monitors and wants to configure them all to have the same settings. Currently, the bedside monitors include hundreds of options, such as the number of electrocardiogram (EKG) channels, the language of the display, alarm levels, patient parameters to be monitored, and the like. The monitors include a video screen with pop-up windows through which a person can select these various options. However, selecting among the hundreds of options can be time-consuming.

To mitigate laborious and time-consuming configuration of multiple devices, software is designed and provided to the monitors 12 to enable them to read configuration settings from barcodes. For instance, monitors can be updated with barcode configuration read/write software using a USB stick or other input means. In one embodiment, a booklet includes all of the settings codes in a barcode format. In another embodiment, the software is reconfigured such that one of the monitors can be configured to the hospital or ward standard, and then a series of barcodes that describe the configuration is printed out. A paper strip with these printed barcodes can then be read by each of the other monitors, which will respond to the barcodes by adopting the same configuration. If the monitors 12 are networked, the configuration information can also be transmitted over a network. As an alternative to the barcode, the settings can be transferred between monitors using other types of portable memory devices, such as a USB stick, CD, floppy disk, etc. In still other embodiments, the monitors can print patient charts with a snapshot of the sensor readings, or the like. Patients can be identified on such printouts by the patient ID barcode, without a human-readable patient name, in order to preserve privacy and confidentiality.

Still referring to FIG. 1, the system 10 includes a first vital signs monitor 12a and a second vital signs monitor 12b, collectively referred to herein as "monitor 12," except where independently described. Each monitor 12 is coupled to a barcode scanner 14, labeled as respective barcode scanners 14a and 14b in FIG. 1. However, it will be appreciated that a single barcode scanner may be utilized with multiple monitors if desired. For instance, a technician or user can decouple the barcode scanner from the first monitor and then couple it to the second monitor as desired.

According to an embodiment, a user or clinician configures the first monitor 12a using one or more of a variety of techniques. For instance, the user can configure the first monitor using a GUI (not shown) on the monitor, which provides a series of menus from which the user selects options (e.g., number of EKG channels, patient parameters to monitor such as blood pressure, heart rate, $SpO_2$, temperature, $CO_2$, respiration, etc., or the like) to configure the monitor. Additionally or alternatively, the monitor has installed software that provides barcode-reading capability, and the user scans one or more barcodes using the barcode scanner 14a, each barcode representing a portion of configuration information. For instance, the user can be provided with a booklet or other printout of multiple barcodes that the user scans to configure a given parameter of the monitor. According to an example, the user is guided through configuration by identifying a desired configuration for the monitor and then scanning corresponding barcodes to achieve the desired configuration.

To further the above example, the user may desire that heart rate, blood pressure, and respiration rate are presented the monitor, and that an alarm sounds when any of the parameters exceeds a predetermined upper or lower bound. As used herein, "exceeds" can mean, for instance, that the monitored patient parameter rises above an upper threshold value, or conversely, falls below a lower threshold value, or both. In this sense, the alarm is triggered whenever the monitored patient parameter is outside of a predetermined acceptable range. According to an example, the alarm may be triggered when the patient's blood pressure is too high or too low, when the patient's temperature is too high or too low, etc. The user can scan a barcode associated with each of the desired parameters in the booklet, and optionally can scan a second barcode for each parameter to turn on the alarm function. Additionally, the user can be presented with one or more barcodes related to values for each parameter, which the user scans to set the alarm condition boundaries, including the selected numerical values for the thresholds discussed above. Alternatively, the threshold values are keyed in manually on the first monitor via the pop-up windows.

Once the first monitor 12a is configured, the custom configuration information is provided to the second monitor 12b. According to one embodiment, the user proceeds to the second monitor and re-scans the same barcodes to configure the second monitor with the same configuration as the first monitor. Alternatively, the user scans a predefined set of barcodes to enter a standard configuration into all monitors 12, and then scans one or more unique barcodes into each monitor. In this manner, each monitor is provided with a standard configuration while permitting customization desired for individual patients' needs.

Additionally, each monitor 12 includes a memory 16 and a processor 18 that facilitate storing and executing commands associated with barcode reading, configuration information, patient information, and any other information storage and/or routine execution germane to providing the functionality described herein. In one embodiment, the monitor stores its custom configuration in a memory 16, and a user prints out a hard copy of the configuration as a series of barcodes. In this case, the monitor has software that permits encoding configuration information, including the selected threshold values, in barcode format. The user then takes the barcoded configuration information from the first monitor to the second monitor and scans in the sequence of barcodes to configure the second monitor the same as the first monitor. This process may be repeated multiple times to configure as many monitors as desired in a given healthcare facility or a portion thereof. In some embodiments, only the first monitor has print-out capability, and the printed configuration codes are printed once and scanned at each subsequent monitor. In other embodiments, each monitor has a printer 20 associated with it and the user can print barcoded configuration information from any monitor when the need to configure an additional monitor arises. In one embodiment, the printer is a strip chart recorder, which may be integral to the monitor or external thereto.

According to an embodiment, the monitor is coupled to a user input device 22, which permits a user to input information (e.g., vital signs threshold levels to trigger one or more alarms, etc.), and one or more inputs 24 that are attached to a patient to sense vital sign information. The monitor additionally includes a display 26 that displays vital sign information to a user, such as a clinician, nurse, physician, etc. In this embodiment, the processor 18 is a configuration processor or the like, which executes instructions for configuring the monitor and/or barcode reader 14.

In an example, a plurality of inputs 24 receive one or more of a plurality of vital sign readings, and forward the vital sign information to the monitor, where the memory 16 records the vital sign readings. The user input device (e.g., a mouse, stylus, one or more control knobs, buttons, keys, etc.) is employed by a user to set one or more threshold levels that trigger an alarm to sound to alert a nurse or the like that the patient requires attention. For instance, the user input device can be used to set an acceptable range of blood pressure values, such that if the patient's blood pressure exceeds the upper limit or falls below the lower acceptable limit for a predetermined amount of time, the alarm is triggered. The user employs the barcode reader 14 to scan barcodes comprising configuration information for the monitor, and the configuration processor configures the monitor to receive selected vital signs, to activate selected threshold levels for one or more of the selected vital signs. Additionally, the configuration processor receives configuration instructions from one or both of the user input device and the barcode reader. Once configured, the configuration information is stored to the memory and the printer 20 prints the configuration information in barcode format, for scanning in and configuring other monitors.

Figure 2:
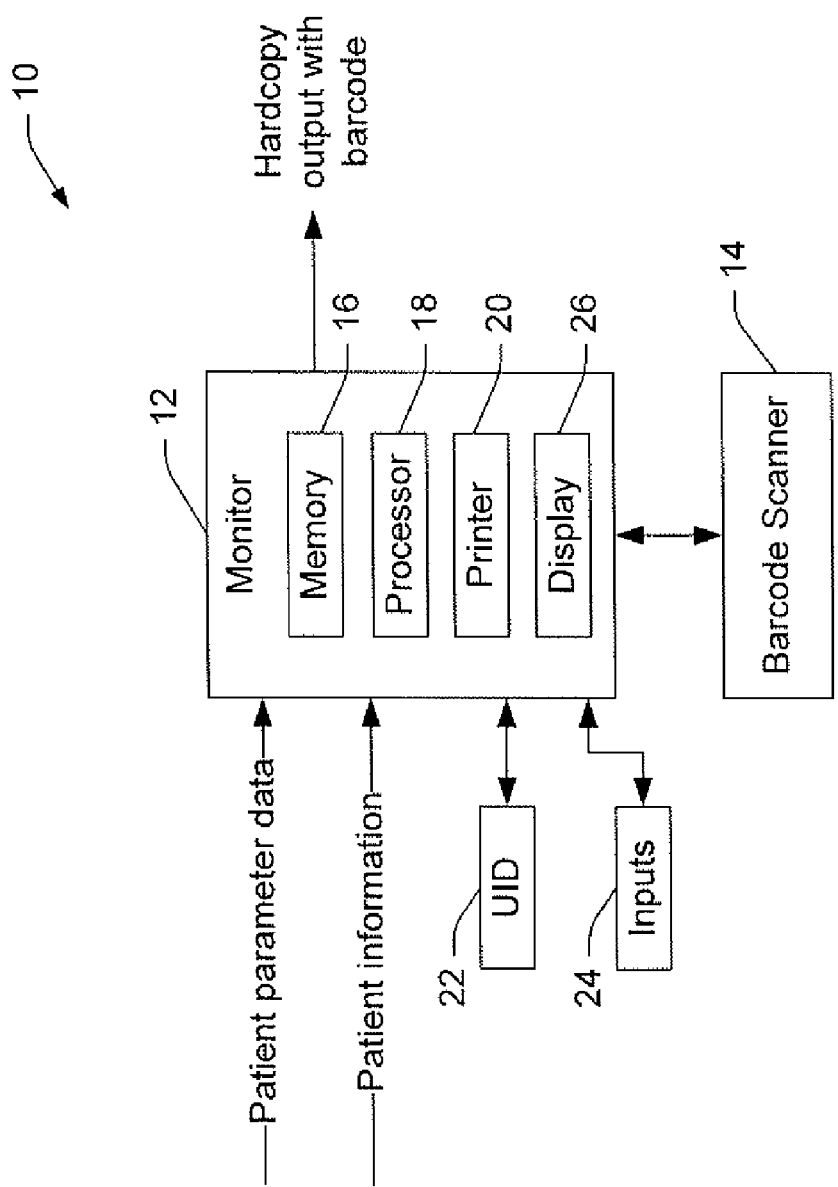
FIG. 2 illustrates the system, as used for printing a patient ID barcode to a hard copy output from the monitor, in accordance with various aspects presented herein.

FIG. 2 illustrates the system 10, used for printing a patient ID barcode to a hard copy output from the monitor 12, in accordance with various aspects presented herein. In this manner, the user prints a barcode for the patient ID information, rather than a human-readable name, to facilitate increasing confidentiality and privacy. The use of the barcode also provides speed and ease of use for the clinician. The system includes the vital signs monitor 12, which is coupled to the barcode scanner 14, such as integral in the same housing, by a cable, and/or by a wireless communication link (e.g., Bluetooth, Zigbee, etc.). The monitor includes the memory 16, processor 18, and printer 20, as described above. Patient information is input to the monitor from a variety of sources. For instance, patient information can include the patient's identification information, which may be manually entered by a user or clinician, or may be scanned in from a barcoded wristband or the like using the barcode scanner. Additionally, patient parameter data is received by the monitor, such as from physiological status sensors attached to the patient. Such parameters can be current, historical, hourly, daily, weekly, etc., graphs, trends, or the like, and can include blood pressure, heart rate, $SpO_2$, EKG information, $CO_2$, blood-glucose levels, or any other monitored parameter. The monitor presents the received patient parameter data on a GUI (not shown). However, when a user desires to print out a record (e.g., strip chart) of the monitored parameter data, the user indicates such to the monitor (e.g., by pressing a "print screen" button, by selecting a "continuous print" mode for a strip chart, or the like) and the printer prints out the record with the barcode ID of the patient to whom the monitor is connected. Although the patient ID is barcoded for confidentiality, the physiological parameter information may be in human-readable form. Patient ID information is scanned into the monitor from a barcode wristband or the like when the monitor is connected to the patient, and the ID information is stored in the memory.

According to another embodiment, the printout request is triggered by an alarm condition, such as a monitored parameter exceeding a predetermined upper or lower threshold level for the parameter. In this case, the alarm is triggered, and a record (e.g., a strip chart, etc.) of the monitored parameters at the time of the alarm is printed out with the patient's barcoded ID information. Thus, if a clinician arrives at the patient's room and the alarm condition is no longer present, the clinician has a hard copy record with the patient's ID on it to evaluate the patient's condition. In a related embodiment, the record is printed by a printer remote from the monitor, such as a nurse's station or the like, so that a user can scan the patient's barcode (or identify the patient in some other manner, such as by room number or the like) on the printed record and identify the patient with the alarm condition.

Software routines for decoding and/or encoding various types of barcode formats are stored in the memory 16, and executed by the processor 18 when needed to read or write information (e.g., patient ID, configuration information, etc.) in barcode format. The printer 20 then prints the desired information in barcode format. For instance, patient ID information is printed as a barcode on a record, such as a strip chart, so that the patient to whom the record pertains is readily identifiable while personal information (e.g., name, age, medical condition(s) is not readily discernable to the human eye. According to other embodiments, such as described above with regard to FIG. 1, the printer prints a hard copy of barcodes describing configuration information for reading by another monitor that is to be configured in the same manner as the first monitor.

Figure 3:
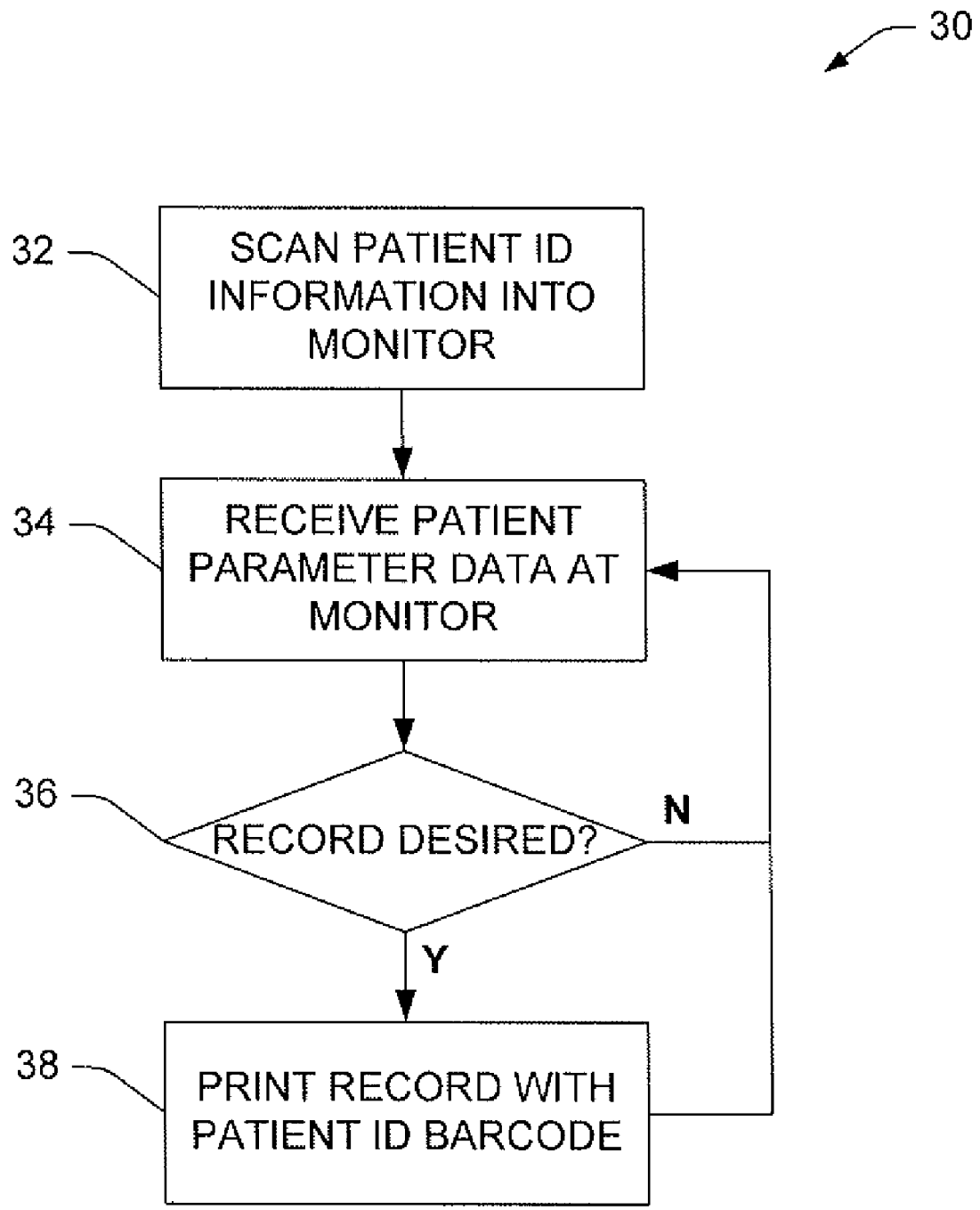
FIG. 3 illustrates a method for operating the system.
Figure 4:
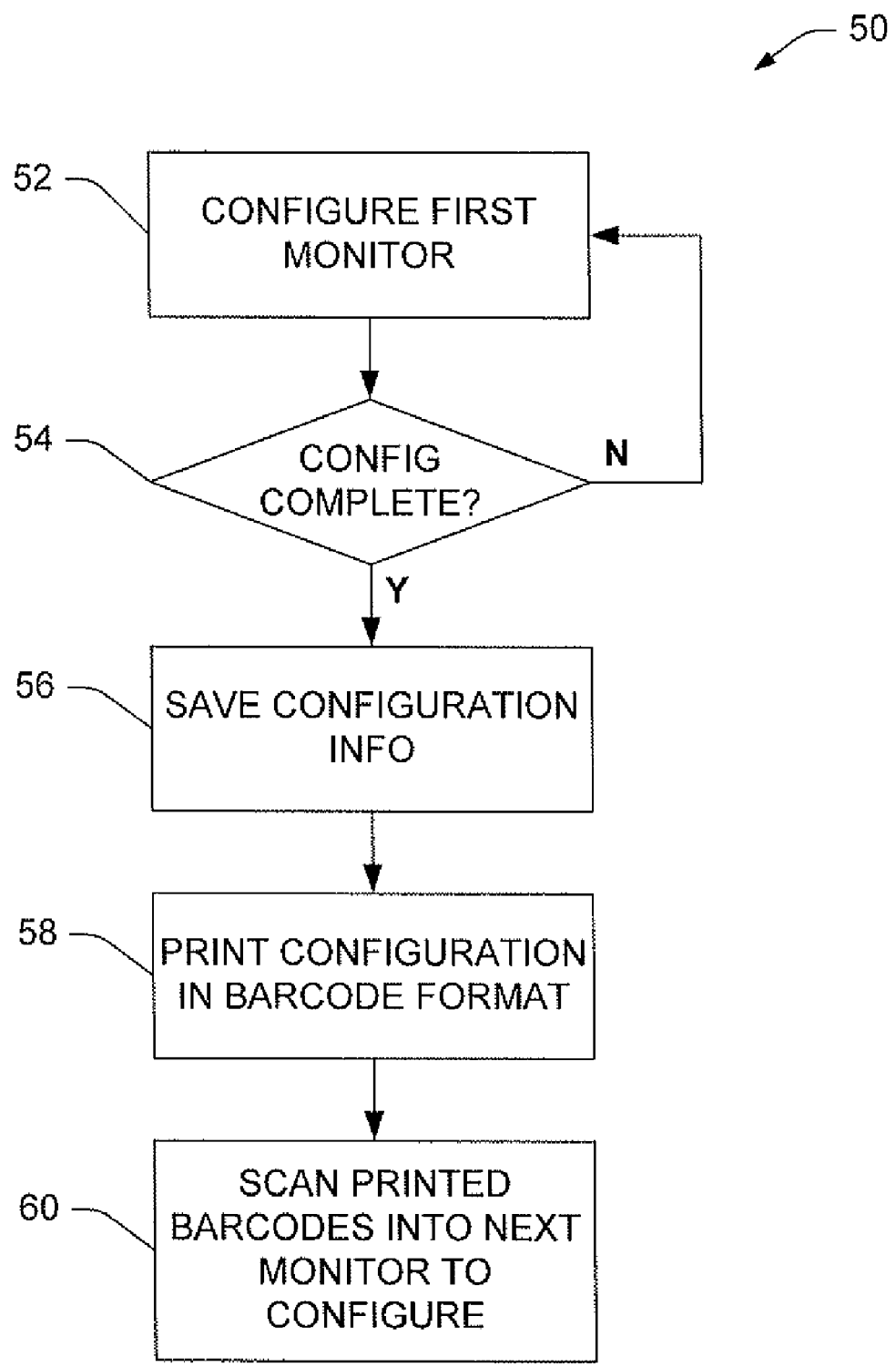
FIG. 4 is an illustration of a method for configuring multiple monitoring devices in a healthcare environment using barcoded configuration information, in accordance with one or more features.

FIGS. 3-4 illustrate one or more methods related to configuring multiple monitoring devices while protecting privacy-sensitive information using barcodes, in accordance with various features. While the methods are described as a series of acts, it will be understood that not all acts may be required to achieve the described goals and/or outcomes, and that some acts may, in accordance with certain aspects, be performed in an order different that the specific orders described.

FIG. 3 illustrates a method 30 for operating the system 10. At 32, patient ID information is scanned into a patient vital signs monitor that is currently or imminently connected to a patient. According to one embodiment, the ID information is scanned into monitor using a barcode scanner coupled to the monitor to read a barcode on a wristband on the patient. In another embodiment, the patient ID information is manually entered into the monitor (e.g., using a keyboard, drop-down menus, etc.). At 34, patient parameter data is received at the monitor. For instance, leads connected to the patient can monitor one or more parameters associated with patient condition, included but not limited to $SpO_2$, blood pressure, heart rate, respiration rate, temperature, $CO_2$, blood-glucose levels, or any other desired parameter that may be monitored.

At 36, a determination is made regarding whether a strip chart record of the patient's vital signs is desired (e.g., whether a user or clinician has entered a "print screen" command, etc.). If no print screen command has been issued, the method reverts to 34, and the patient is continuously monitored. If the user has entered a print screen command, then at 38, the record corresponding to the time of the print request is printed, along with a barcode representing the patient's ID information. For instance, the barcode can be printed in a region of the record where it does not obstruct graphical information related to a monitored parameter. If the user's ID information was manually entered, the monitor can employ software routines to convert the patient ID into barcode format. If the patient ID information was scanned in from a patient barcode on the patient's wristband, then the input barcode can be printed on the printout.

In accordance with another embodiment, the printout request is triggered by an alarm condition, such as a monitored parameter exceeding a predetermined upper or lower threshold level for the parameter. In this case, an alarm may be triggered, and a record (e.g., a strip chart or the like) corresponding to the parameter(s) that triggered the alarm is printed out with the patient's barcoded ID information. Thus, if a clinician arrives and the alarm condition is no longer present, the clinician has a hard copy record with the patient's ID on it to evaluate the patient's condition. In some embodiments, the record is printed remotely from the monitor, such as a clinician's desk or the like, so that a clinician can scan the patient's barcode on the printed record and identify the patient with the alarm condition.

FIG. 4 is an illustration of a method 50 for configuring multiple monitoring devices in a healthcare environment using barcoded configuration information, in accordance with one or more features. At 52, a first monitor is configured. Configuration of the first monitor may be performed manually (e.g., entering configuration information via conventional means), by a USB memory stick with configuration stored thereon, and/or by scanning a series of barcodes representing configuration information. For instance, a user or clinician is provided with a booklet containing barcodes, each of which represents configuration information for a specific portion of monitor operation, and the user places the monitor in "barcode configuration mode" (e.g., by selecting an option from a menu or the like) and scans the barcodes using a barcode scanner to input the configuration information. For example, if the healthcare provider desires that all monitors in its facility are configured to present heart rate and blood pressure information but not respiratory information, then a user scans the barcodes identified in the booklet as enabling the heart rate and blood pressure parameters to be monitored and displayed and does not scan a barcode identified as enabling the respiration rate to be displayed, etc. At 54, a determination is made regarding whether configuration is complete. For instance, a "configuration complete" barcode can be presented in the booklet for the user to scan once all configuration barcodes have been scanned. As long as this barcode is not entered into the monitor, the method reverts to 52 for continued configuration. In this manner, the monitor continuously watches for the configuration-complete barcode while being configured.

If the determination at 54 indicates that configuration is complete for the monitor, then at 56, the configuration information for the monitor is saved to persistent memory. Configuration information is then printed as a series of barcodes (e.g., the series of barcodes that was entered to configure the monitor is and printed), at 58. For instance, the user selects a "print barcodes" option from a menu or the like. The user then places a new monitor in barcode configuration mode and scans the barcodes using a bar code scanner coupled to the new monitor, at 60. In this manner, the user only refers to the booklet during configuration of the initial monitor, and then rapidly scans the printed-out barcodes related to the desired configuration of the remaining monitors. According to another embodiment, the user scans the barcodes from the booklet for each monitor configuration.

Figure 5:
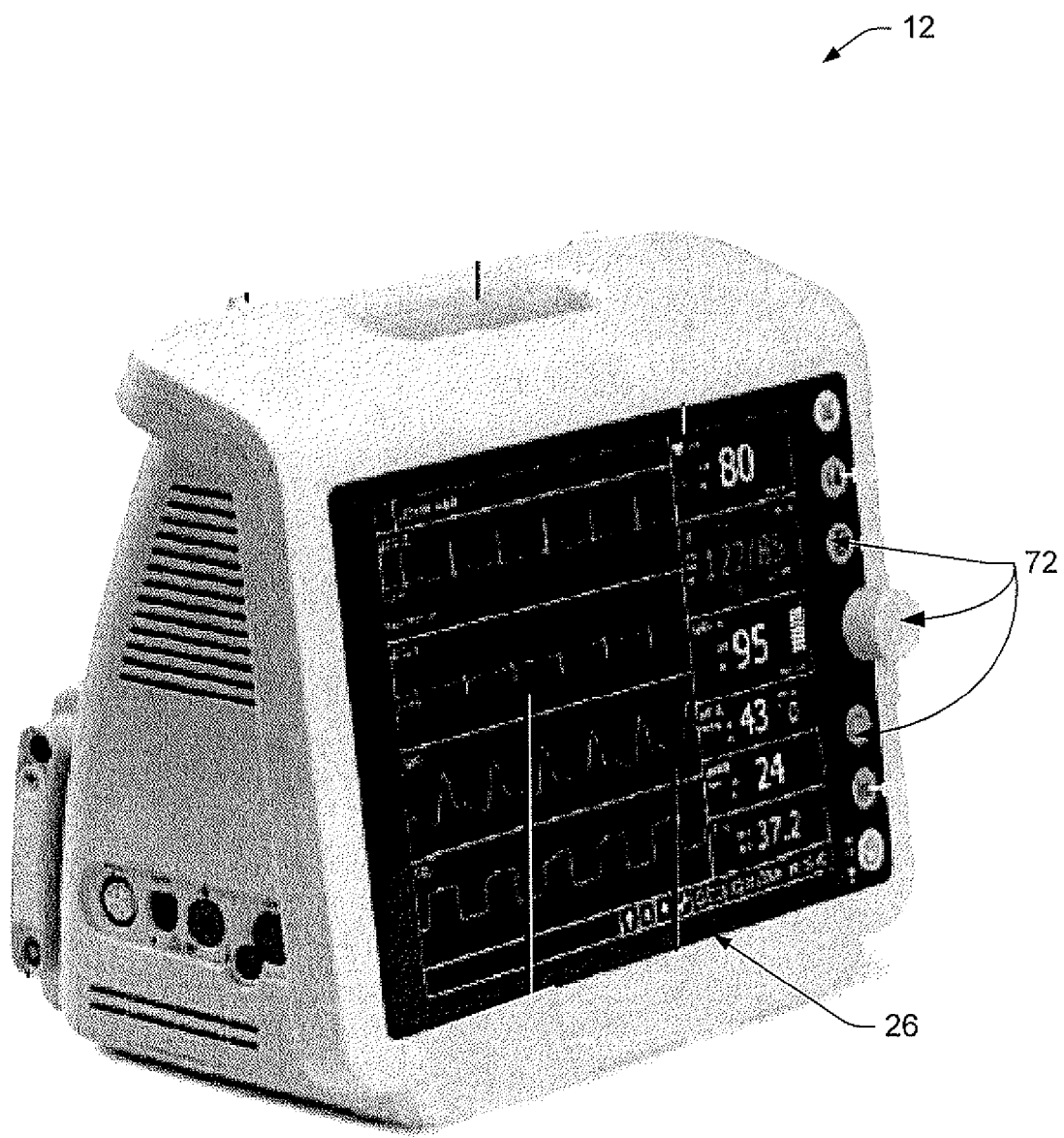
FIG. 5 is an illustration of a vital signs monitor, such as can be employed in conjunction with the systems and/or methods described above.

FIG. 5 is an illustration of a vital signs monitor 12, such as can be employed in conjunction with the systems and/or methods described above. The monitor 12 comprises a screen or display 26 that displays information to a user. For instance, the screen can display vital sign information related to a patient to whom the monitor 12 is connected. The monitor 12 also has a plurality of control components 72, such as buttons, knobs, and the like, which are employed by a user to select information for viewing, to manipulate a given view of the screen, etc. It will be appreciated that the monitor 12 can monitor any and all suitable or desired patient-related conditions, including but not limited to blood pressure, temperature, heart rate, $SpO_2$, exhaled $CO_2$, blood-glucose levels, electrocardiogram (ECG) related information, etc.

The monitor can be configured using the systems and/or methods described above. For instance, configuration information can be entered to the monitor using a barcode scanner (not shown) to scan one or more configuration information barcodes. The barcodes can be scanned from a booklet comprising a complete set of configuration barcodes as well as from a printout of configuration barcodes from another monitor. The latter barcode source permits more rapid configuration information entry because a user need not flip through redundant or irrelevant barcodes that comprise configuration information that may not be required for a desired configuration.

Having thus described the preferred embodiments, the invention is now claimed to be:

1. A system for configuring multiple patient monitors, including:
   a first vital signs monitor;
   a first barcode scanner that reads configuration barcodes comprising configuration information and provides the configuration information to the first vital signs monitor; and
   a printer that generates a printout of configuration barcodes comprising information related to the configuration of the first vital signs monitor upon a determination that the configuration of the first vital signs monitor is complete.

2. The system according to claim 1, further including a second vital signs monitor with a second barcode scanner, wherein a user enters configuration information into the second vital signs monitor by scanning the configuration barcodes on the printout.

3. The system according to claim 2, further including a set of printed configuration barcodes from which a user selects barcodes for scanning.

4. The system according to claim 3, further including a user input device for manually entering configuration information.

5. The system according to claim 1, wherein the barcode scanner is operable to scan a patient ID barcode of a patient is connected to the monitor.

6. The system according to claim 5, wherein the printer prints a record of a monitored patient parameter having the patient ID barcode thereon, the record being devoid of a human-readable identification of the patient.

7. The system according to claim 6, wherein the vital signs monitor includes a vital signs input through which at least one of blood pressure, heart rate, respiratory rate, $CO_2$, $SpO_2$, temperature, or blood-glucose level, of the patient is received, and a display on which at least one of the received vital signs is displayed.

8. The system according to claim 6, wherein the printer is triggered to print the record by at least one of the user or the monitored patient parameter exceeding a predetermined upper or lower threshold value.

9. The system according to claim 1, wherein the processor includes:
   a routine or means for configuring the first monitor;
   a routine or means for determining when monitor configuration is complete;
   a routine or means for printing configuration information in barcode format; and
   a routine or means for scanning the barcoded configuration information into at least a second vital signs monitor.

10. The system of claim 1, further including a USB memory stick having configuration information stored thereon, which is inserted into the first vital signs monitor to configure the first vital signs monitor.

11. A method of configuring multiple vital signs monitors, including:
    configuring a first vital signs monitor;
    storing configuration information in the first vital signs monitor when configuration is complete;
    printing the stored configuration information in the form of one or more barcodes; and
    configuring a second vital signs monitor by scanning the printed barcodes with a second barcode scanner coupled to the second vital signs monitor;
    wherein configuring the first vital signs monitor further includes at least one of scanning one or more barcodes including configuration information, which are selected from a pre-printed set of barcodes, or inserting a USB memory stick with configuration stored thereon into the first vital signs monitor; and
    further including manually entering vital signs threshold values through a user interface, the manually entered threshold values being printed in barcode format during the printing step.

12. The method according to claim 11, further including scanning a patient ID barcode on a patient's wristband of the patient connected to the vital signs monitor.

13. The method according to claim 12, further including printing out a vital signs record from the first vital signs monitor with the patient ID barcode on the record and with a human-readable patient identifier.

14. The method according to claim 13, wherein the vital signs record is a strip chart including graphical vital sign information.

15. The method according to claim 13, further including printing the record in response to at least one of a user request for the record or an alaiin condition detected at the monitor.

16. The method of claim 11, wherein the vital sign threshold value defines a threshold value of at least one of blood pressure, heart rate, respiratory rate, $CO_2$, $SpO_2$, temperature, or blood-glucose level, of the patient.

17. A processor or computer-readable memory programmed to perform the method of claim 11.

18. A system that facilitates configuring multiple patient monitoring devices, including:
means for configuring a first patient monitoring device;
means for storing configuration information upon determining that the configuration of the first vital signs monitor is complete;
means for printing barcodes comprising configuration information; and means for configuring a second patient monitoring device by scanning the printed barcodes.

19. A patient monitor comprising:
a plurality of inputs for receiving each of a plurality of vital sign readings;
a memory for recording the received vital sign readings;
a user input device;
a barcode reader;
a configuration processor for configuring the monitor to receive selected vital signs, and threshold values for at least some of the selected vital signs, the configuration processor being connected with the barcode reader and the user interface to receive configuration instructions therefrom; and
a barcode printer connected with the configuration processor to print, upon a determination that configuration of the monitor is complete, configuration instructions for other monitors in barcode format.

\* \* \* \* \*